(12) United States Patent
Fernandes et al.

(10) Patent No.: US 10,647,181 B2
(45) Date of Patent: May 12, 2020

(54) PREDICTIVE SCENT CONTROL SYSTEM AND METHOD THEREOF

(71) Applicant: Continental Automotive GmbH, Hannover (DE)

(72) Inventors: Brian Sunil Nicholas Fernandes, Singapore (SG); Thomas Johann Jablonski, Regensburg (DE)

(73) Assignee: Continental Automotive GmbH (DE)

( * ) Notice: Subject to any disclaimer, the term of this patent is extended or adjusted under 35 U.S.C. 154(b) by 0 days.

(21) Appl. No.: 16/479,057

(22) PCT Filed: Jan. 19, 2017

(86) PCT No.: PCT/EP2017/051016
§ 371 (c)(1),
(2) Date: Jul. 18, 2019

(87) PCT Pub. No.: WO2018/133933
PCT Pub. Date: Jul. 26, 2018

(65) Prior Publication Data
US 2019/0366809 A1    Dec. 5, 2019

(51) Int. Cl.
*B60H 3/00* (2006.01)
*A61L 9/14* (2006.01)
(Continued)

(52) U.S. Cl.
CPC .............. *B60H 3/0035* (2013.01); *A61L 9/14* (2013.01); *B60H 1/008* (2013.01);
(Continued)

(58) Field of Classification Search
CPC ...... B60H 3/0035; B60H 1/00742; A61L 9/14
See application file for complete search history.

(56) References Cited

U.S. PATENT DOCUMENTS

| 5,297,738 A | 3/1994 | Lehr et al. |
| 6,357,726 B1 | 3/2002 | Watkins |
(Continued)

FOREIGN PATENT DOCUMENTS

| CN | 101722819 A | 6/2010 |
| DE | 20302097 U1 | 7/2003 |
(Continued)

OTHER PUBLICATIONS

International Search Report and Written Opinion for International Application No. PCT/EP2017/051016, dated Sep. 29, 2017—9 pages.

*Primary Examiner* — Kevin Joyner
(74) *Attorney, Agent, or Firm* — RatnerPrestia (57) ABSTRACT

A predictive scent control system and method thereof for dispersing a scent into a passenger compartment of an automotive based upon a feedback system having a decision unit and a set of predefined users' settings. Dispersion of scent or fragrance into the passenger compartment may be based upon prediction user behavioural profile. User behavioural profile may include an average based upon timing of access to vehicle, an average based upon frequency of selection of predefined user settings, and an ambience of the passenger compartment. In another embodiment, the predictive scent control system may be configurable to disperse a pungent scent in the event of unauthorised access to the vehicle. The predictive control system is applicable to vehicles for multiple users or car-sharing.

16 Claims, 7 Drawing Sheets

(51) Int. Cl.
*B60H 1/00* (2006.01)
*B60R 25/01* (2013.01)

(52) U.S. Cl.
CPC ..... *B60H 1/00742* (2013.01); *B60H 1/00971* (2013.01); *B60R 25/018* (2013.01); *A61L 2209/111* (2013.01); *B60H 2003/0064* (2013.01)

(56) References Cited

U.S. PATENT DOCUMENTS

| | | |
|---|---|---|
| 2008/0006651 A1 | 1/2008 | Arakawa et al. |
| 2012/0107172 A1 | 5/2012 | Ono et al. |
| 2019/0176768 A1* | 6/2019 | Diaz Garcia ............ A61L 9/14 |

FOREIGN PATENT DOCUMENTS

| | | |
|---|---|---|
| EP | 0483848 A2 | 5/1992 |
| GB | 2521929 A | 7/2015 |
| JP | 06227248 A | 8/1994 |
| JP | 2000060949 A | 2/2000 |

\* cited by examiner

PREDICTIVE SCENT CONTROL SYSTEM AND METHOD THEREOF

CROSS REFERENCE TO RELATED APPLICATIONS

This application is the U.S. National Phase Application of PCT International Application No. PCT/EP2017/051016, filed Jan. 19, 2017, the contents of such application being incorporated by reference herein.

FIELD OF INVENTION

A predictive scent control system and method thereof for dispersing a scent into a passenger compartment of an automotive based upon a feedback system having a decision unit and a set of predefined users' settings. Dispersion of scent or fragrance into the passenger compartment may be based upon user behavioural profile.

BACKGROUND OF INVENTION

There are many existing fragrance control devices that automatically disperse a predetermined amount of scent into the atmosphere of an enclosed environment.

By way of example, EP 483848 B1, incorporated herein by reference, with a date of filing of 31 Oct. 1991 discloses a vehicle installed fragrance supplying apparatus which is programmed to release an amount of scent based on predetermined operating cycles.

US 2012107172 A1, incorporated herein by reference, with a date of filing of 10 Jun. 2014 discloses a fragrance device for a vehicle and a method of blowing the fragrance to distribute the fragrance within interior of the vehicle. Using a control means, the fragrance is repeatedly circulated within an enclosed compartment at a predetermined time period.

GB 2521929 A, incorporated herein by reference, with a date of filing of 21 Nov. 2014 discloses a fragrance diffusing unit and method for operating such unit for a vehicle. An embodiment of GB 2521929 A includes dispensing a fragrance when a signal for vehicle access control is received.

None of the above prior art documents discusses the use of a fragrance control system for dispersing aroma, scent or fragrance within a vehicle passenger compartment according to users' preferences to increase user experience and/or comfort.

SUMMARY OF INVENTION

Moreover, with the increasing challenges of vehicle access security issues, an aspect of this invention aims to implement a predictive scent control system that serves as a form of deterrence against breach of vehicle access security.

There is therefore a need for a predictive scent control system that will address to the above discussed problems.

Predictive is a well-known term of art and thus readily understood by those skilled in the art.

According to the *Cambridge Advanced Learner's Dictionary & Thesaurus*, predictive is:

used to describe a computer system that predicts what is wanted or needed. For example:

Predictive word processors are useful for those who have trouble with typing or spelling.

Predictive cruise control uses GPS technology to determine the exact position of the vehicle and to know which driving conditions have to be taken into account.

An aspect of this invention is a predictive scent control system that aims to solve the above discussed problems.

To accomplish this and other aspects of this invention, in a first aspect of an embodiment, there is provided a predictive control system for dispersing a scent within a passenger compartment of a vehicle. The predictive control system comprising a first module for controlling functions of the vehicle; a second module in communication with the first module, the second module being configured for receiving radio frequency signals from an access system of the vehicle to enable access to the vehicle; a third module for housing a plurality of containers or vials, each of the plurality of containers or vials containing a different scent; and a feedback system for dispersing a scent into the passenger compartment of the vehicle. The feedback system further comprises (a) a programmable controller for sending a first notification when triggered by a decision unit; (b) an air sampling mechanism being configured for collecting a sample of the air from the passenger compartment; and (c) a feedback subsystem in communication with the programmable controller, the second module and the third module. The word "vial" shall be construed to mean small containers for holding or containing fluid such as aroma oils or perfume and it shall be further understood that the terms "vial(s)" and/or "container(s)" refers to the same item in the context of this patent document.

The advantage of the configuration of the above discussed embodiment is the implementation of a module, i.e. the feedback system comprising of a feedback subsystem and a decision unit that allows collecting information of the ambient of a passenger department of a vehicle, such as mood of the passengers, collecting a sample of the air from the passenger compartment to determine if more scent is required to maintain a specific concentration of fragrance or scent in the environment, and/or make predictive decisions based upon computation of an average, an arithmetic mean, a median or a rate of recurrence of users' selection, behavioural profile of user(s) such rate of recurrence of access to vehicle at specific timing, selection of fragrances, amongst others.

The predictive control system is applicable to vehicles for multiple users or car-sharing. In a car sharing example, when a first user access the vehicle and enters the passenger compartment, the second module detects the location of the first user. This is communicated to the decision unit which in turn sends a notification to the third module and the first user's preferred scent or fragrance is dispersed into the passenger vehicle. When the first user exits the vehicle, the second module locates the first user is outside of the vehicle. The decision unit is triggered and programmable controller exhaust or de-fragrance the passenger compartment. When a second user access and enters the passenger compartment, the process is repeated.

In another multiple users embodiment, the predictive fragrance control system is configured to detect mood within the passenger compartment using visual cameras and/or seat biometrics, thus detecting the mood of different user in the driver seat in real-time, thereby dispersing a suitable scent or fragrance that matches with the user's preceding state of mind.

Alternatively, the predictive fragrance control system is configured to collect a sample of the air from the ambient of the passenger compartment to control the intensity or concentration of scent within the passenger compartment. In a multiple user scenario, e. g. a plurality of users enters the passenger compartment and one of the plurality of users is heavily scented or perfumed. By collecting a sample of the air from the passenger compartment, the intensity or concentration of the scent or fragrance within the passenger compartment is being regulated.

Preferably, the decision unit is in communication with the first module and the third module. This allows the decision unit to communicate an instruction or a notification to the first and third modules.

Preferably, the feedback system sends a first notification for dispersing an amount of scent upon receiving a set of predefined instructions from an input control. The set of predefined instructions receivable from the input control includes a selection of (a) an amount of scent to be dispersed into the passenger compartment based upon a set of predefined preferences; (b) an amount of scent to be dispersed into the passenger compartment based upon at least one user's preferences; (c) an amount of scent to be dispersed into the passenger compartment based upon a condition of the access system of the vehicle; and (d) a time—based cycle for the amount of scent to be dispersed into the passenger compartment. Examples of possible predefined preferences include default factory settings and/or a plurality of users' preferred settings.

The air sampling mechanism is configured for identifying a concentration of the scent within the air based on the sample of air collected. This allows the decision unit to give instruction to the feedback system for dispersing an amount of fragrance or scent into the ambient of the passenger compartment.

The feedback subsystem is configured for sending a second notification to the programmable controller, instructing the feedback system to disperse an amount of scent into the passenger compartment if the concentration of the scent within the collected sample of the air does not match with a predetermined concentration value.

In a second aspect of an embodiment, the predictive scent control system includes a second module providing an input to the feedback subsystem when an unauthorised access to the vehicle is detected.

In the event an unauthorised access to the vehicle is detected, the feedback system disperses a disturbing or pungent scent into the passenger compartment. The objective of using the pungent scent serves as a deterrence to keep intruder from vehicle theft is thereby achieved. Preferably the scent contains a unique substance creating a unique scent or smell and enabling to identify or tag a person. Another advantage of releasing the disturbing or pungent scent in the event of unauthorised access to the vehicle is scent tagging, where the disturbing or pungent scent stays on the fabric of an intruder, thus trained police dogs is able to track the intruder. In addition, the disturbing or pungent scent deters the intruder from staying in the vehicle and driving away the vehicle.

In a third aspect of an embodiment, a method of operating a predictive control system for dispersing a scent within a passenger compartment of a vehicle according to the implementation of an aspect of this invention, including a decision unit is configured for producing a decision based upon a behavioural profile of at least one user in the passenger compartment.

Preferably, the behavioural profile is according to a first statistical mean of a first recording corresponding to a timing of access to the passenger compartment. An advantage of the first arithmetic means is to predict the frequency of a user accessing the vehicle, to predict or forecast at which timing of a day the user gains accesses to his or her vehicle.

Alternatively, the behavioural profile is according to a second statistical mean of a second recording corresponding to a selection from the set of predefined instructions received by an input control. This second statistical mean is used for prediction or forecasting a user's selection of the set of predefined settings, to determine choice of scent to disperse. It shall be understood, the terms "a mean", "an arithmetic mean", "a median", "a statistical mean" or "standard deviation" all refers to an average of a range of readings or recordings obtained. The term "correlation" shall be construed to be a statistical procedure for determining the degree of similarity between at least two types of variables, for eg. date and time.

Additionally, the behavioural profile can also be defined by detection of mood within the passenger compartment. The determination of mood within the passenger compartment based upon facial recognition technique, using image processing technology. Other possible parameters for detection of mood include choice of music or even lighting within the passenger compartment.

The advantage of the aforesaid method achieves the objective of operating a predictive scent control system according to user's behavioural profile.

DESCRIPTION OF PREFERRED EMBODIMENTS

Figure 1:
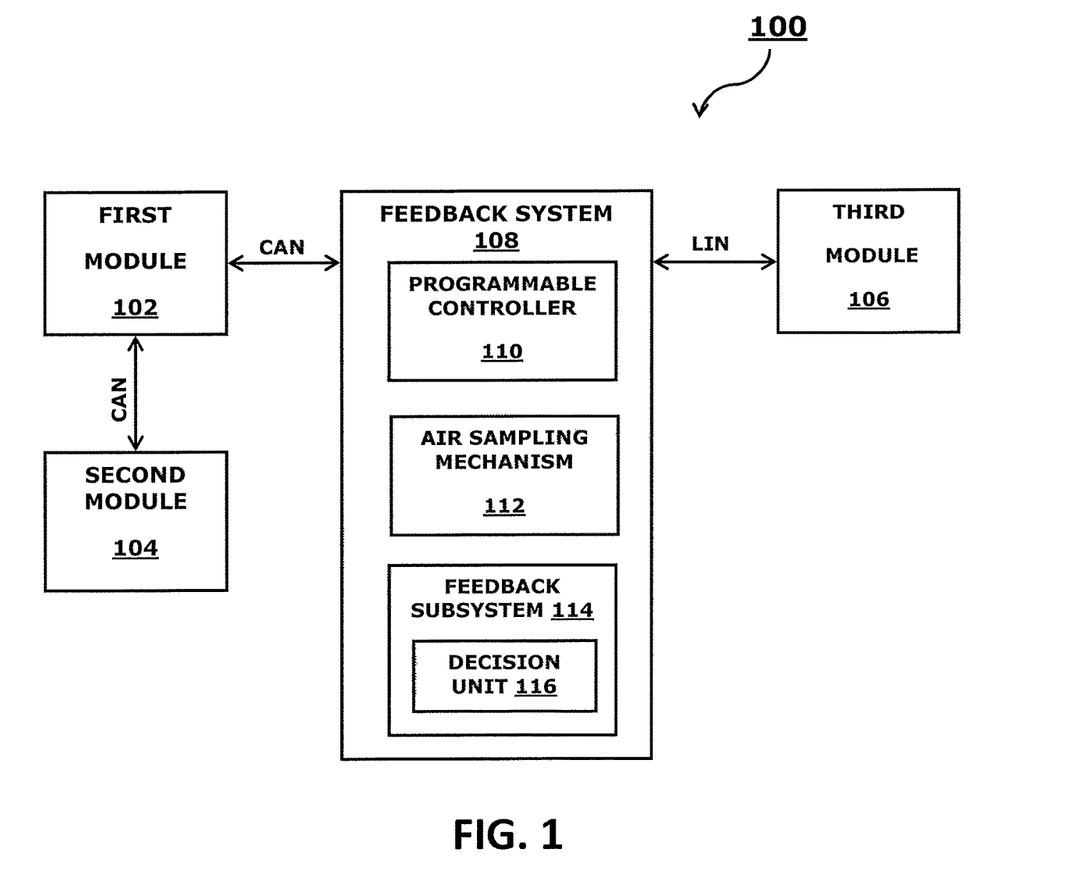
FIG. 1 shows the block diagram of an aspect of the system architecture of an aspect of this invention.

FIG. 1 shows a block diagram illustrating vehicle system architecture 100 showing the configuration and the relative functions of the modules using a bus network, such as controller area network (CAN) or local interconnect network (LIN). Other suitable types of network includes RF communication, Ethernet or fibre optics. It will be understood by a person skilled in the art that similar types of bus networks are applicable.

In a preferred embodiment, the first module 102, such as a body control module, is configured for controlling functions of the vehicle. The second module 104 allows receiving radio frequency (RF) signals from a remote controller such as a key fob. The second module 104 is being configured to be in communication with the first module 102 of the vehicle. It will be understood by a person skilled in the art that such configuration is state of the art for vehicle access control.

The third module 106 is for housing a plurality of vials, each of the plurality of vials containing a different scent, fragrance, aroma, perfume or essential oil. Ideally, the different scents is blended in the third module 106 to provide customisable fragrance or scent according to user's preference. The fragrance or scent in each of the vial can be in the form of solid, fluid or gaseous state. For example in fluid state, it can be essential oils, or perfume that can be atomize when dispersed into air. In another preferred embodiment, the scents contained in the plurality of vials is blended to disperse a pungent scent in the event of a breach of security.

The feedback system 108 is configured for controlling dispersion of a scent into the passenger compartment of the vehicle. The feedback system 108 comprises of a programmable controller 110 for sending a first notification when triggered by a decision unit 116. In addition, the feedback system 108 has an air sampling mechanism 112 being configured for collecting a sample of the air from the passenger compartment. The feedback system further comprises a feedback subsystem 114 in communication with the programmable controller 110, the second module 104 and the third module 106. In alternative embodiment, the air sampling mechanism can also include an active suction device or flow control device to enable a larger quantity of air to be collected for sampling.

Figure 2:
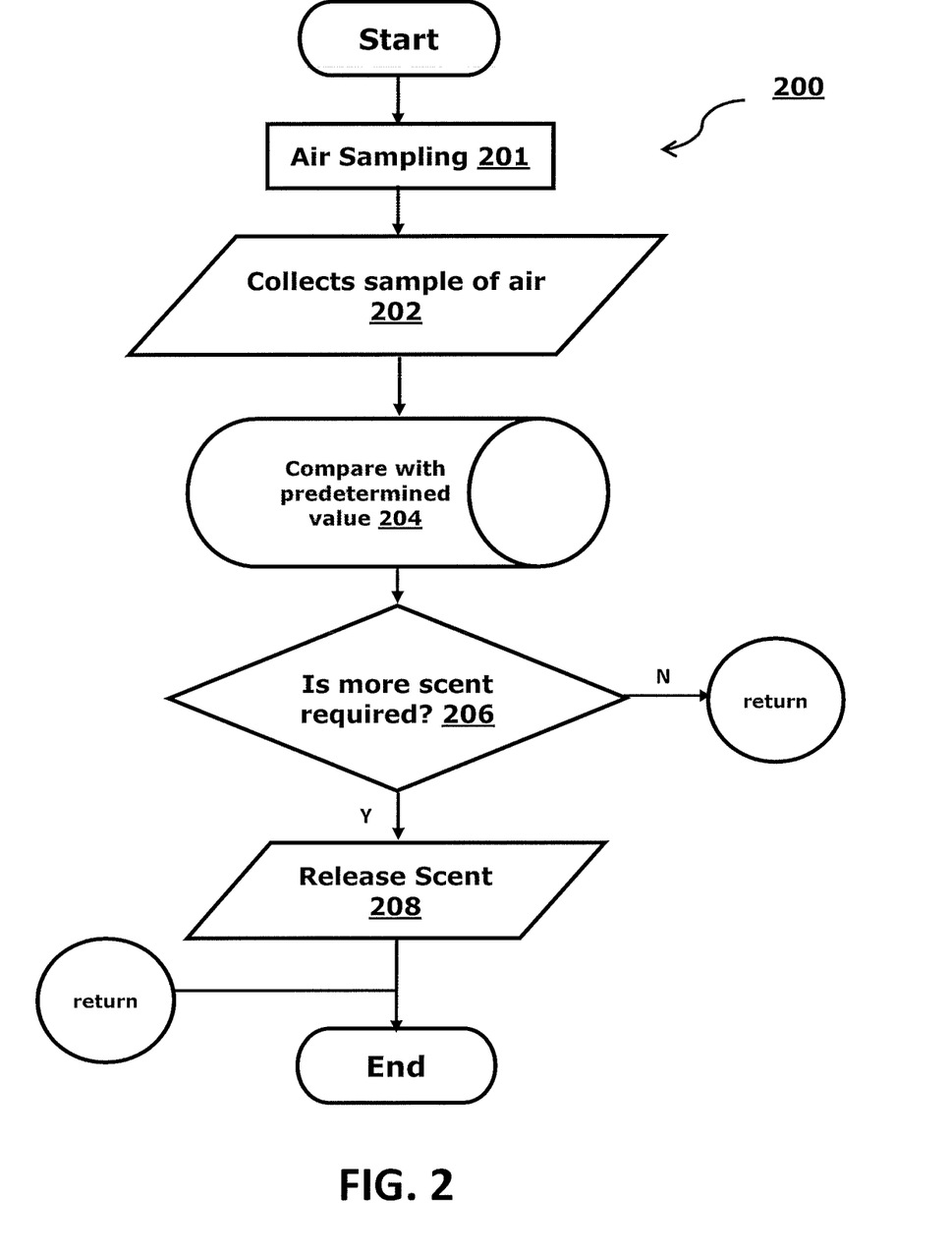
FIG. 2 illustrates a system flowchart of an aspect of the algorithm of a feedback control unit in a preferred embodiment.

FIG. 2 shows a system flowchart 200 of an air sampling algorithm or method of a decision unit 116 of the feedback subsystem 114 of the feedback system 108 to achieve the implementation of an aspect of this invention. In step 201, air sampling process begins when the air sampling mechanism 112 collects a sample of the air 202 from the passenger compartment. The concentration of scent in the sample of air collected from the passenger compartment is used to benchmark or compare against a predetermined value 204 to ensure that there are sufficient particles per million (ppm) of scent, aroma or fragrance within the ambient of the passenger compartment. Step 206 executes a decision on whether more scent is required in the ambient of the passenger compartment is programed to determine if the concentration of scent in the sample of air falls below the predetermined concentration value 204, step 208 is activated to release scent into the ambient of the passenger compartment. Otherwise, in the event that the concentration of scent in the sample of air does not fall below the predetermined value 204, no amount of scent will be released into the ambient of the passenger compartment. The air sampling algorithm is to monitor and identify the density of different compounds in the sample of air and heuristically identify the composition of the scent or aroma in the air so that a comparison or benchmark can be made to identify whether more scent or aroma needs to be released. The programmable controller 110 is configurable to be in communication with the second module 104 and third module 106, and the decision unit 116 is configurable to be in communication with the first module 102 and third module 106. The air sampling algorithm achieves a distributed dispersion of aroma in the passenger compartment and thus enhancing comfort and user experience.

When implemented, the feedback system 108 sends a first notification for dispersing an amount of scent upon receiving a set of predefined instructions from an input control. The set of predefined preferences includes default factory settings and/or a plurality of users' preferred settings. A selection of the settings is activated via an input control.

The feedback subsystem 114 is configured for sending a second notification to the programmable controller 110, instructing the feedback system 108 to disperse an amount of scent into the passenger compartment if the concentration of the scent within the collected sample of the air 202 does not match with a predetermined concentration value 204. It will be understood the measurement of concentration value is in the form of particles per molecule (ppm).

Figure 3:
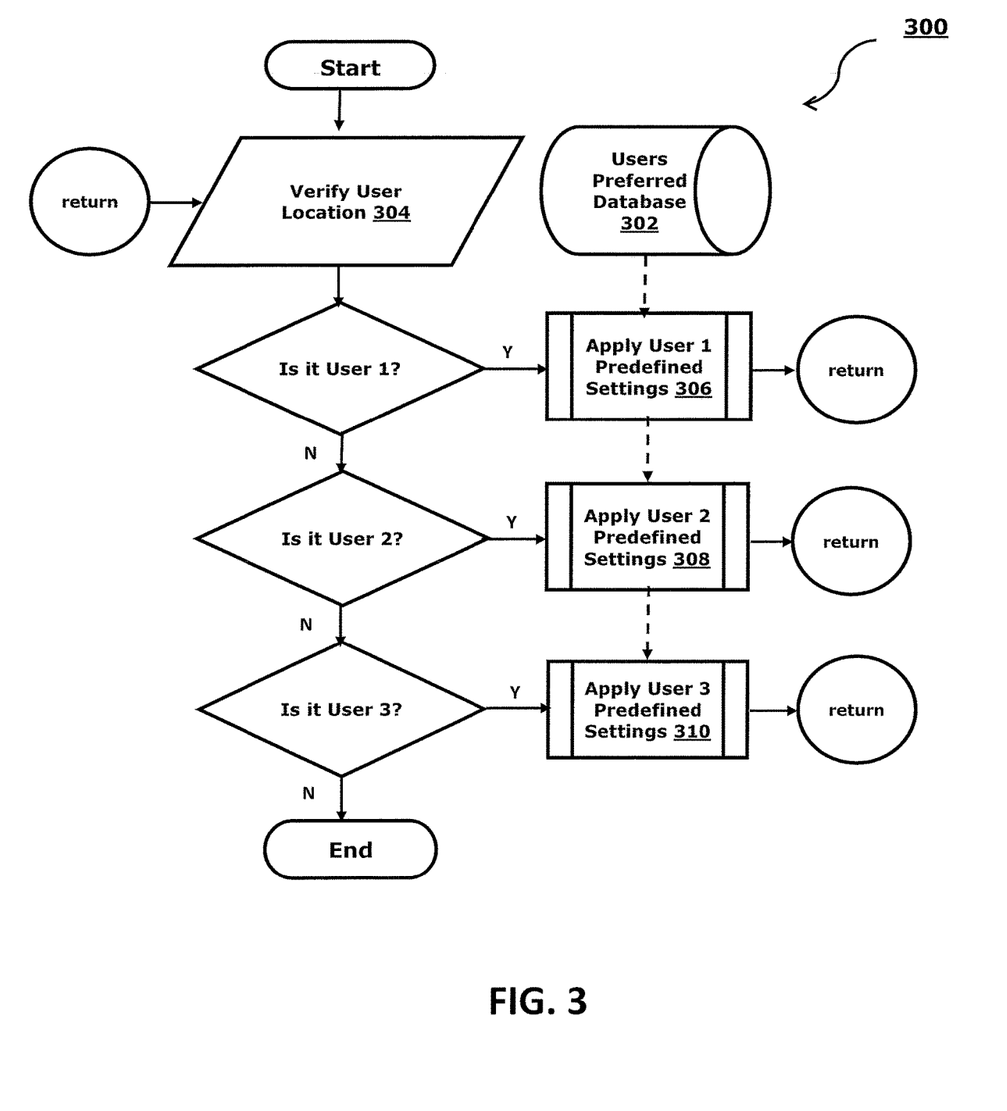
FIG. 3 illustrates a system flowchart for selecting aroma based upon a programmable database of users preferences.

In an alternative embodiment, dispersion of user's preferred aroma or scent is configured according to a user preference database 302, according to user's predefined input. With reference to FIG. 3, the selection of predefined instructions from an input control is programmable and stored in a user preference database 302 for multi-user access, which is activated when the user access the vehicle. In step 304, the second module 104 verifies the location of a user entering the passenger compartment. A users' preference database 302 stores information of users' preferences. The aforesaid information can be based upon user's predefined settings or choice of scent or aroma. Once step 304 is executed, specifics of the user preference is determined. The decision unit 116 executes step 306 to determine whether it is User 1 who has entered the passenger compartment. If User 1 is determined, step 308 executes the application of User 1 predefined settings. If step 306 does not matches the aforesaid condition, the decision unit 116 executes step 310 to determine if it is User 2 who has entered the passenger compartment. If it is verified in step 306 that the user who has entered the passenger compartment is User 2, step 312 is executed to apply User 2 predefined preferred settings. In the event that it is determined at step 310 the user who has entered the passenger compartment is not User 2, the decision unit 116 moves on to step 314 to determine if it is User 3 who has entered the passenger compartment. At step 314, if the user is determined to be User 3, predefined preferred settings of User 3 applies and so forth.

To further clarify the above process, for instance, when a user, e. g. User A, access the vehicle in the morning, User A sends a signal to the first module 102, which in turn notifies second module 104 to locate User A. This can be done using localisation technics known in the art, for example, locating a keyless entry device through signal communication between the second module and the keyless entry device, for eg. a key fob, a mobile phone, etc. The second module 104 executes the step of 304, to verify location of User A and feedback system 108 triggers the programmable controller 110 to send a notification to disperse User A's preferred aroma based on the user preference database 302. In the step of 306, when User A exits the passenger compartment, the programmable controller 110 de-fragrance the passenger compartment, allowing execution of a second preferred aroma or scent to be released when a second or another user, for eg. User B enters the passenger compartment.

Figure 4:
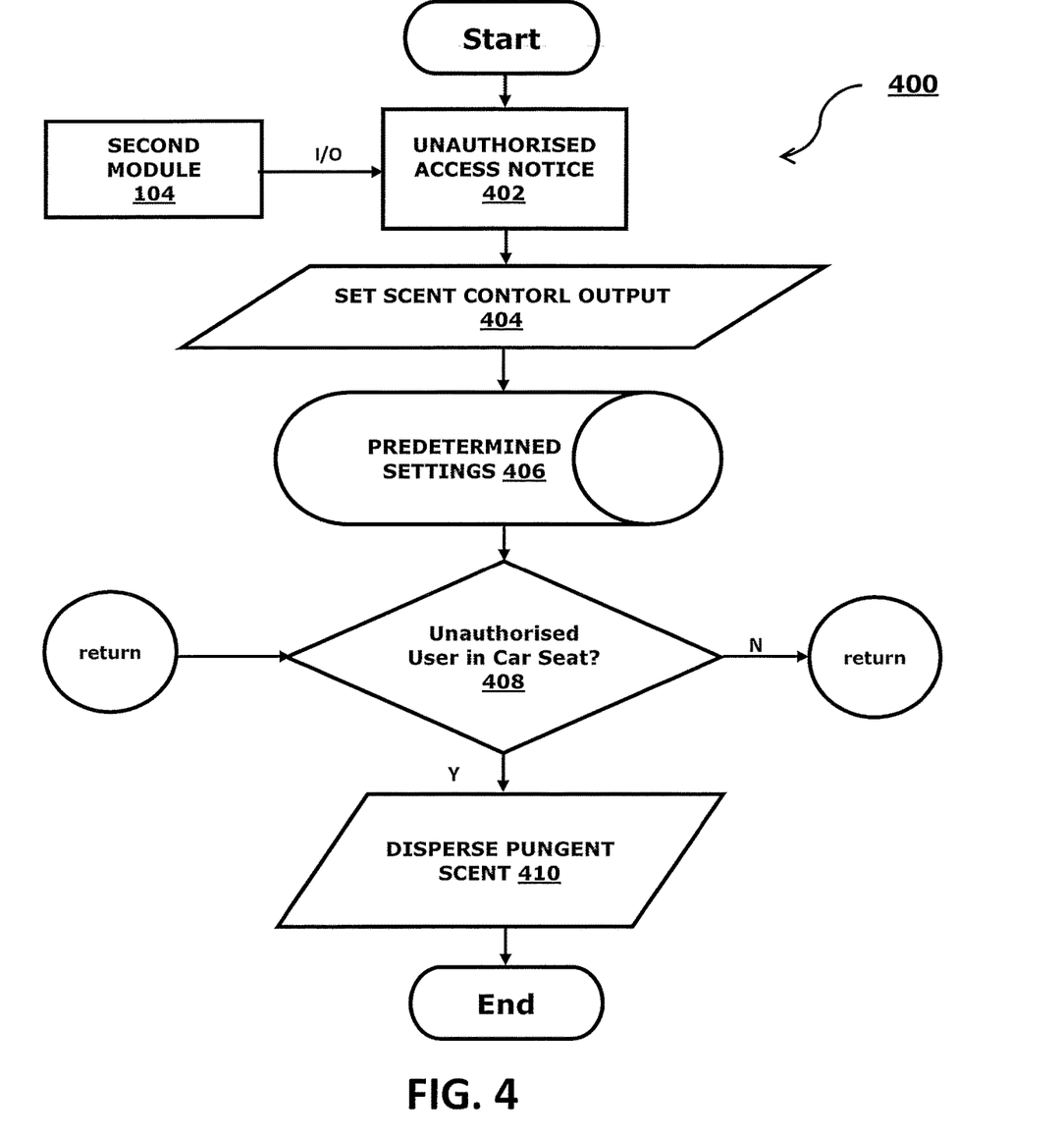
FIG. 4 illustrates a system flowchart for controlling dispersion of a pungent scent in the event of an unauthorised access to vehicle.

In a second aspect of the preferred embodiment, the second module 104 is configured to provide an input to the feedback subsystem 114 when an unauthorised access to the vehicle is detected. This process is shown in FIG. 4, which illustrates a system flowchart 400 for controlling dispersion of a pungent scent in the event of an unauthorised access to vehicle or passenger compartment.

When an unauthorised access to the vehicle is triggered or detected by second module 104, the feedback system 108 sends an unauthorised access notice 402 to set scent control output 404 to disperse a pungent scent into the passenger compartment, configurable by a predetermined settings 406 to blend the pungent scent. In step 408, the programmable controller 110 verify if the signals received by the second module 104 is the owner of the vehicle. Other information based upon RF fingerprinting, voice recognition or facial recognition technology can be configured for verification purposes. If the verification fails, the third module 106 which houses the plurality of vials containing the aroma, essential oils or perfume is configured to blend the pungent scent. The decision unit 116 of the feedback system 114 commands instruction to disperse a pungent scent 410. The objective of using a predictive scent control system as deterrence against vehicle theft is thereby achieved. Otherwise, the system returns to determine a polling rate or statistical mean 502, 502' after a predefined interval.

Figure 5A:
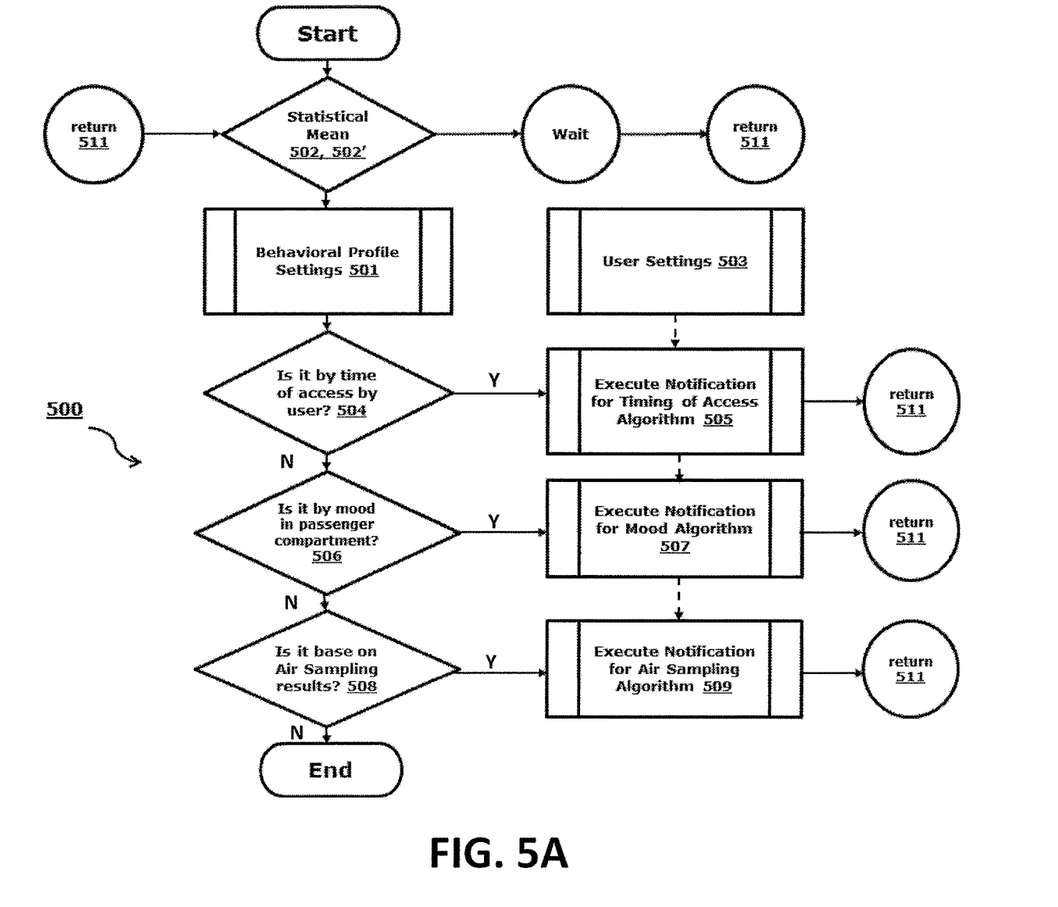
FIG. 5A illustrates a system flowchart for controlling dispersion of scent according to a user behavioural profile.

Referring now to FIG. 5A, which shows another preferred embodiment, a method of operating a predictive control system for dispersing a scent within a passenger compartment of a vehicle according to the implementation of an aspect of this invention includes a decision unit 116 configured for producing a decision based upon a behavioural profile 501 of at least one user in the passenger compartment. It shall be appreciated that prediction or forecast behavioural profile 501 is not restricted to driver, but also other users of the vehicle or passengers of passenger compartment.

FIG. 5A illustrates a system flowchart 500 explaining the criteria required to determine behavioural profile 501 relative to a polling rate or statistical mean 502, 502'. It will be understood the behavioural profile 501 is a decision derived from predetermined rules, parameters and/or algorithms defined when designing the predictive scent control system based upon user's preference, default factory settings and even design of passenger compartment. In step 502, 502' of FIG. 5A, a decision is made to compute value of a statistical mean. Once a value of the statistical mean 502, 502' is computed, the decision unit 116 decides on the behavioural profile settings 501 to determine the applicable algorithm to execute. Examples of predetermined rules, parameters and/or algorithm as shown in FIG. 5A includes user settings 503, time of access by user 504, mood in passenger compartment 506 and air sampling results 508.

In an aspect of this embodiment, the behavioural profile settings 501 is according to a first statistical mean 502 of a first recording corresponding to a timing of access by a user 504, or entering the passenger compartment by a user. In this scenario, the decision unit 116 executes the computation of statistical mean in step 502. Decision unit 116 verifies whether the behavioural profile settings 501 is in accordance to the time of access by the user. If it is verified by the second module 104 that the time of access of vehicle by user coincides with a correlated timing of vehicle access, step 505, the decision unit 116 executes a notification relative to timing of access algorithm, commanding an instruction to the feedback system to disperse an amount of scent or aroma into the ambient of the passenger compartment. Upon executing the time of access algorithm, the system returns to step 511 and the system begins to verify the polling rate or statistical mean 502, 502'.

In the event that the step 504 does not coincide with the correlated timing of access by user, the decision unit 116 applies the next predetermined rule as shown in step 506, to determine mood of users in passenger compartment coincides with the mood in the passenger compartment. If rule 506 applies, the decision unit 116 executes a notification for mood algorithm 507 to take effect and the vice versa applies. Once the mood algorithm 507 is executed, the system returns to step 511 to verify the polling rate or statistical mean 502, 502'.

In the event step 506 does not apply to the passengers in the passenger compartment, then the decision unit 116 applies the next rule, i.e. step 508, to determine if the decision is based upon air sampling results and execute step 509 to notify the feedback system 108 to execute an air sampling algorithm. Again, upon executing the air sampling algorithm, the system returns to step 511 to verify the polling rate or statistical mean 502, 502'.

The behavioural profile 501 is derived according to a second statistical mean 502' of a second recording corresponding to a selection from the set of predefined instructions received by an input control. An input control can be in the form of control buttons either within the vehicle, via a remote controller or via a human machine interface (HMI). This second statistical mean 502' is obtained to predict or forecast a user's selection of the set of predefined settings, to determine for example, choice of fragrance to disperse.

It will be understood a statistical mean 502, 502' can be achieved through polling evaluation. By way of example, a range of recordings of the time of a user's access to the vehicle is recorded. This recording can be in the range of calendar days, to record for eg. timing of user's access to the vehicle. The recordings is evaluated or analysed to obtain a statistical mean 502, 502' to forecast the approximate timing of a user's access to the vehicle on any particular day. This statistical mean 502 is configured for dispersing an amount of scent or fragrance into the passenger compartment, as a welcome scent when the user, operator or driver accesses the vehicle. A timing of access algorithm 505 is in turn communicated to the second module 104, to command decision unit 116 of the feedback system 108 to disperse an amount of scent into the passenger compartment based upon the timing of access algorithm 505.

The above implementation is useful and applicable to multi user or car sharing. By way of example, a first user, User 1 wish to enter the vehicle. In order to do so, User 1 is required to press an input control button on a key fob or alternatively, activate an access control from a mobile phone to access the vehicle. This will require the second module 104 to locate the position of User 1. Once the second module 104 identifies the location of User 1, the decision unit 116 triggers a notification to the programmable controller 110 which will in turn execute time of access algorithm 505 to release User 1's preferred scent into the passenger compartment. When User 1 exits the vehicle, the second module 104 locates position of User 1 is outside of the vehicle and thus the programmable controller 110 exhaust or de-fragrance the passenger compartment, allowing execution of a second preferred aroma or scent to be released when a second or another user. Base on the system flow as shown in FIG. 5A, the process return 511 and thus the system repeats the process of verifying the polling rate or statistical mean 502, 502'. When a second user, i.e. User 2 enters the vehicle, the process is repeated, thereby releasing User 2's preferred scent into the passenger compartment.

In another example using the system flowchart of FIG. 5A, take for instance a user is feeling agitated while driving in a heavy traffic jam. The programmable controller 110 selects a scent associated with calming senses of the user. In a multiple user-scenario, detection of mood can be aided by visual cameras or seat biometrics and detection unit 116 execute notification for mood algorithm 507 to disperse a therapeutic scent into the ambient of the passenger compartment.

In yet another example, the predictive fragrance control system is configured to collect a sample of the air from the ambient of the passenger compartment to control the intensity or concentration of scent within the passenger compartment. In a multiple user scenario, for example a plurality of users enters the passenger compartment and one of the plurality of users is heavily scented or perfume. A decision is made at step 508 based on air sampling results and the decision unit 116 execute notification for air sampling algorithm 509. Once step 509 is executed, the system returns to step 511, and determine a polling rate or statistical mean 502, 502' to identify behavioural profile settings 501.

Figure 5B:
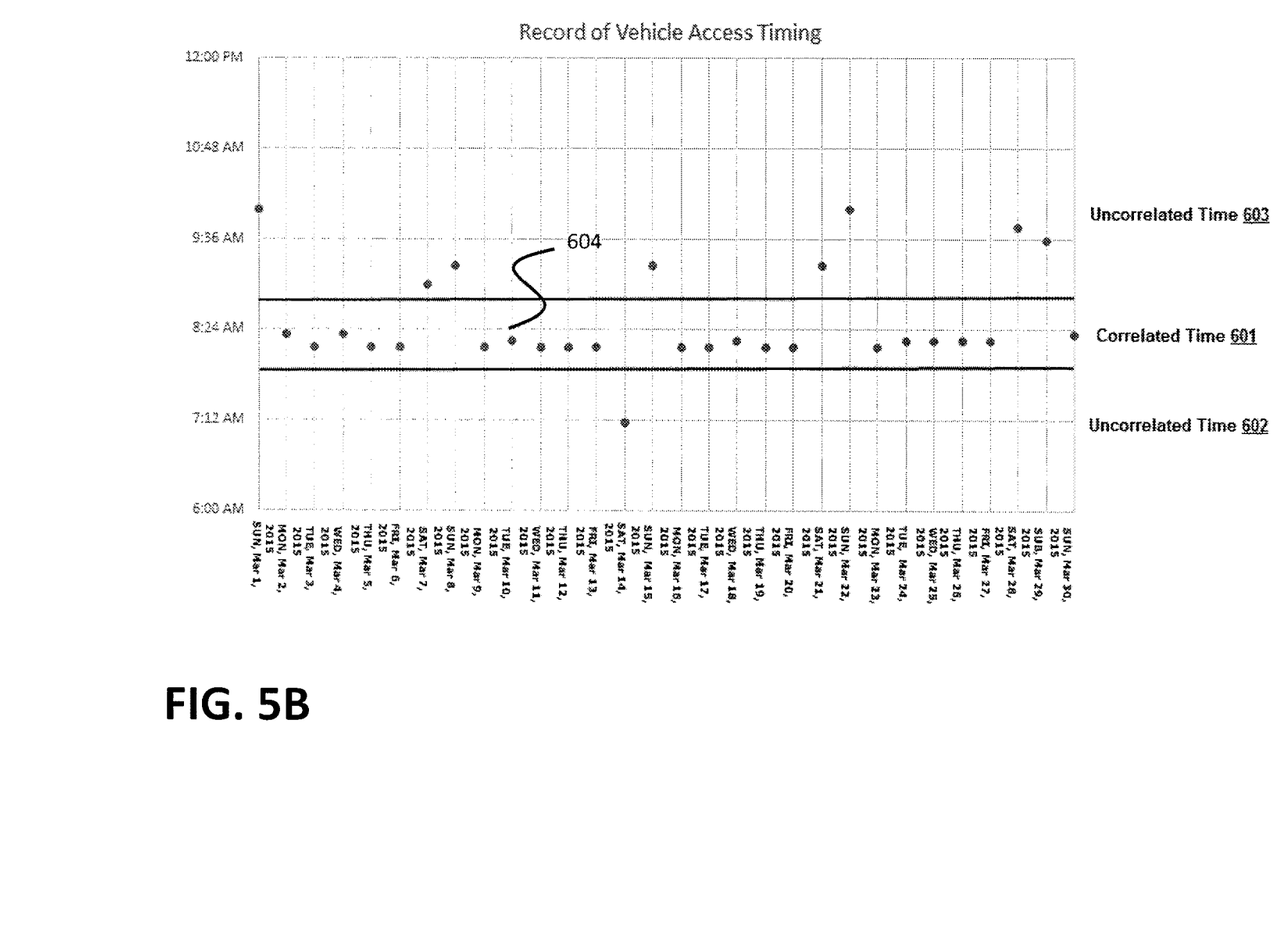
FIG. 5B shows a sample recording of user vehicle access timing according to date and time within one month window, wherein the timings are analyzed for correlation.

FIG. 5B illustrates a sample recording of timing of access 604 to a vehicle by a user every morning for a period of one-month window for prediction or forecasting the time of access to the vehicle by a specific user. The dots 604 in FIG. 5B represent the time of access. The horizontal axis shows the dates. In this example one time of access 604 per day is shown.

However, it will be understood that the recording can save more than one time of access 604 per day. The vertical axis shows the time of the day. It will be understood by a person skilled in the art that sample recordings of timing of access 604 may be based upon short term window, such as the example given in FIG. 5B. Long-term period of X number of months or X number of years is also applicable. In this scenario, the time of accessing 604 the vehicle is recorded according to a calendar month, i.e. between Sunday, Mar. 1, 2015 to Sunday, Mar. 30, 2015. The recurrence of time of access to the vehicle by the user is highest between 8:00 am to 8:30 am, thus there is a high probability that the user access the vehicle between 8:00 am to 8:30 am on a daily basis, based upon this historical data. Applying this method of pattern recognition, the time of access between 8:00 am to 8:30 am is identified as the correlated time 601, and the other recordings of time of access will be categorised as uncorrelated time 602 or 603 as indicated in FIG. 5B. Preferably the correlated time 601 is defined as a time span in a way that a certain percentage of the times of access 604 lies within this time span. Further variables to consider includes day of accessing the vehicle according to the timing categorised as correlated time 601. Clearly, in FIG. 5B, the day of accessing the vehicle under the timings categorised as correlated time 601 falls under Mondays to Fridays or weekdays. Based upon this correlation of day and time of past events, the timing of access can be predicted based upon statistical mean 502, since there is a high probability that the user will access his or her vehicle within a correlated time 601 period typically for 5 out of 7 days, excluding weekends. It shall be understood by a person skilled in the art the recording of FIG. 5B is used to determine the correlated time 601.

In another example, a range of recording of the frequency of selection of predefined user's settings 503 is used for polling evaluation. The user's settings 503 includes selection of specific scent or fragrance or selection of default factory settings such as predetermined time-cycle for dispersing an amount of scent into the passenger compartment. A statistical mean 502, 502' is obtained to predict or forecast the user's desired selection and disperse an amount of the user's preferred scent or fragrance accordingly. The range of recording of the frequency of selection of predefined user's settings 503 is configured according to a frequency or rate of recurrence of selection of a specific scent, for e. g. sporty, romantic, energetic, calming, business, etc. In another example, it is according to a user's preferred default time-based cycle setting such as dispersion of scent every 10 minutes, 15 minutes, etc.

Alternatively, the behavioural profile is defined by detection of mood within the passenger compartment 506. For instance detection of mood can be according to expression of passengers in the passenger compartment. An example of applicable method is facial recognition techniques using interior cameras. For instance the third module 106 is configured to blend a scent or fragrance that is relative to sleepiness to help wake the driver up when the mood of the driver is determined to be sleepy. Other suitable blends of scent or fragrance is relative to mood include sporty, romantic, business, etc. It will be understood different blend of scent or fragrance can be customise and introduced according to users' preferences. A mood algorithm 507 is communicated to the second module 104, to command decision unit 116 of the feedback system 108 to disperse an amount of scent into the passenger compartment based upon the mood algorithm 507. Detection of mood within passenger compartment can leverage on existing technologies, for example, interior cameras that reads and predicts facial expression of passenger(s) and/or driver. Other mood specific functions according to factory settings such as special mood lighting or mood specific functions are applicable for mood prediction.

An air sampling algorithm 509 is implemented to determine the behavioural profile 501 based upon a statistical mean 502 of air sampling results. By way of example, a recording of the air sampling results according to a period of calendar days, weeks or months is recorded to determine how regular does the concentration of the scent within the air in the passenger compartment falls below predetermined concentration value. Using the statistical mean 502 based upon the air sampling algorithm 509, the regularity of air sampling can be adjusted according to the air sampling results. This reading helps to achieve consistent concentration of scent or aroma in the atmosphere of the passenger compartment, thus providing user comfort.

Figure 6:
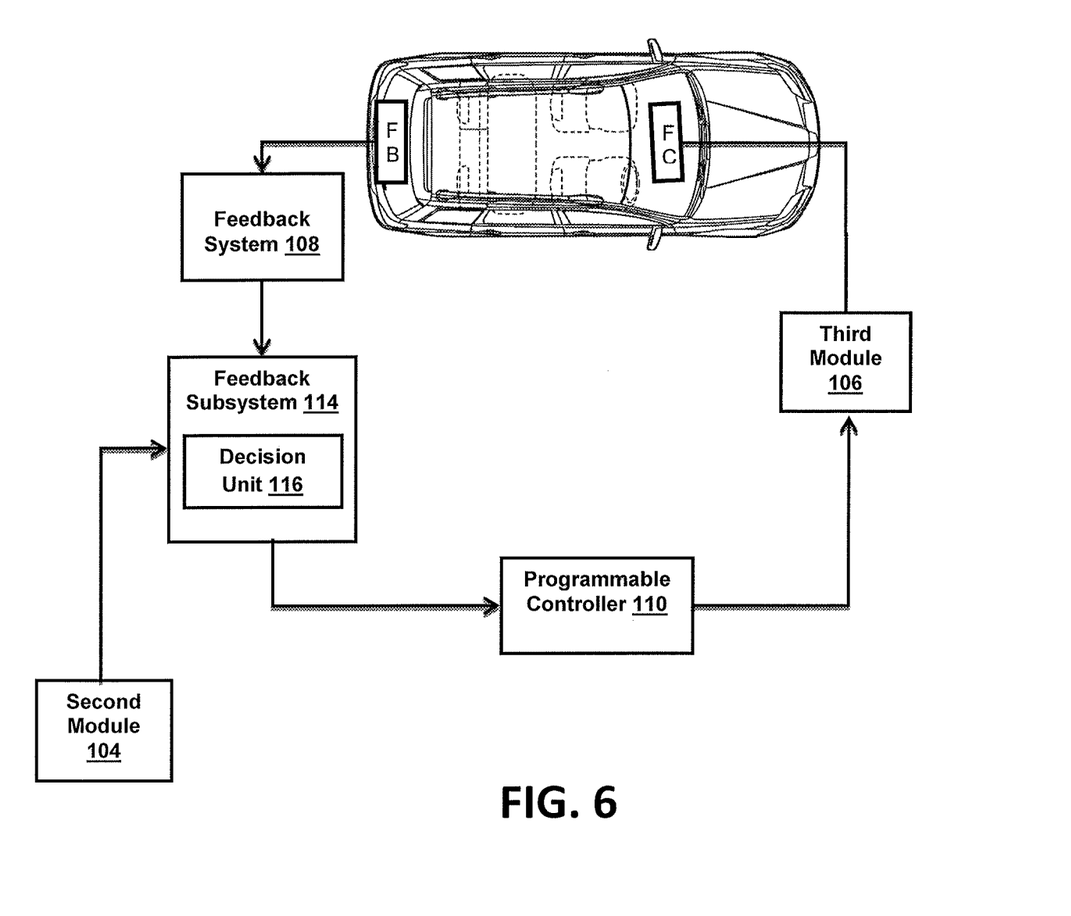
FIG. 6 illustrates an aspect of the preferred embodiment of an aspect of this invention when implemented within a passenger compartment.

FIG. 6 shows the implementation of the system architecture of a preferred embodiment within a passenger compartment. Ideally, the feedback system 108 is connected at the rear of a passenger compartment FB with the third module 106 placed at the front of the passenger compartment FC, in which third module 106 housing the vials will blend and disperse the suitable scent into the atmosphere when atomized, and of feedback system 108 consist of the air sampling mechanism 112 to collect sample of air from the passenger compartment, to optimise the distribution of scent or aroma within the passenger compartment. The feedback subsystem 114 is in communication with the feedback system 108 and the second module 104. When the decision unit 116 triggers a notification to disperse a scent, the notification is sent to the programmable controller 110, which in turn activates the third module 106 to blend a desired scent.

While the preferred embodiment and alternative embodiments of aspects of the invention have been disclosed and described in detail herein, it may be apparent to those skilled in the art that various changes in form and detail may be made therein without departing from the spirit and scope thereof.

The invention claimed is:

1. A predictive control system for dispersing a scent within a passenger compartment of a vehicle, the predictive control system comprising:
a first module configured for controlling functions of the vehicle;
a second module in communication with the first module, the second module being configured for receiving radio frequency signals from an access system of the vehicle to enable access to the vehicle;
a third module for housing a plurality of vials, each of the plurality of vials containing a different scent; and
a feedback system,
wherein the feedback system further comprises:
a programmable controller for sending a first notification when triggered by a decision unit;

an air sampling mechanism being configured for collecting a sample of the air from the passenger compartment; and a feedback subsystem communication with the programmable controller, the second module and the third module.

2. The predictive control system of claim 1, wherein the decision unit is in communication with the first module and the third module.

3. The predictive control system of claim 1, wherein the feedback system sends the first notification for dispersing an amount of scent upon receiving a set of predefined instructions from an input control.

4. The predictive control system of claim 1, wherein set of predefined instructions receivable from the input control includes a selection of:
  an amount of scent to be dispersed into the passenger compartment based upon a set of predefined preferences;
  an amount of scent to be dispersed into the passenger comportment based upon a least one user's preferences;
  an amount of scent to be dispersed into the passenger compartment based upon a condition of the access system of the vehicle; and
  a time-based cycle for the amount of scent to be dispersed into the passenger compartment.

5. The predictive control system of claim 3, wherein the set of predefined preferences includes default factory settings and/or a plurality of users' preferred settings.

6. The predictive control system of claim 1, wherein the air sampling mechanism is configured for identifying a concentration of the scent within the air based on the sample of the air collected.

7. The predictive control system of claim 1, wherein the feedback subsystem is configured for sending a second notification to the programmable controller, instructing the feedback system to disperse an amount of scent into the passenger compartment if the concentration of the scent within the collected sample of the air does not match with a predetermined concentration value.

8. The predictive control system of claim 1, wherein the second module provides an input to the feedback subsystem when an unauthorised access to the vehicle is detected.

9. The predictive control system of claim 8, wherein the feedback system disperses a pungent scent into the passenger compartment when an unauthorized access vehicle is detected.

10. The predictive control system of claim 2, wherein the feedback system sends the first notification for dispersing an amount of scent upon receiving a set of predefined instructions from an input control.

11. A method of operating a predictive control system for dispersing a scent within a passenger compartment of a vehicle according to claim 1, wherein the decision unit is configured for producing a decision based upon a behavioral profile of at least one user.

12. The method of claim 11, wherein the behavioral profile is according to a first statistical mean of a first recording corresponding to a timing of access to the passenger compartment.

13. The method of claim 12, wherein the behavioural profile is according to a second statistical mean of a second recording corresponding to a selection from the set of predefined instructions received by an input control.

14. The method of claim 12, wherein the behavioural profile is defined by a detection of mood within the passenger compartment.

15. The method of claim 14, wherein the detection of mood within the passenger compartment is relative to an ambience of the passenger compartment.

16. The method of claim 14, wherein the detection of mood within the passenger compartment is based upon facial recognition techniques.

* * * * *